United States Patent [19]
Estes et al.

[11] Patent Number: 5,925,802
[45] Date of Patent: Jul. 20, 1999

[54] FUNCTIONAL RECONSTITUTION OF SCID-BO MICE WITH BOVINE FETAL HEMATOPOIETIC TISSUES

[76] Inventors: Don Mark Estes, 805 Colgate; Fred Anthony Mann, 10951 St., Rte. N., both of Columbia, Mo. 65203; Neal Young Brackett, 161 Siniard Rd. NW., Adairsville, Ga. 30103-4746

[21] Appl. No.: 08/473,373

[22] Filed: Jun. 7, 1995

Related U.S. Application Data

[51] Int. Cl.⁶ ..................................................... A61K 48/00
[52] U.S. Cl. ............................ 800/2; 424/93.1; 424/520; 424/582; 424/570
[58] Field of Search ................................. 800/2; 424/520, 424/572, 578, 582, 577, 93.1; 438/1.1, 40.52; 540/545

[56] References Cited

PUBLICATIONS

Boermans et al. "Engraftment of severe combined immune deficient/beige mice with bovine foetal lymphoid tissues," Vet. Imm. and Immunopathology, vol. 34: 273–289, 1992.

Hoffmann–Fezer et al., "Peritoneal sanctuary for human lymphopoiesis in SCID mice injected with human peripheral blood lymphocytes from EBV negative donors," European J. of Immunology, vol. 22 (12): 3161–3166, Dec. 1992.

Sanhadji et al., "Fetal liver cell transplantation in various murine models," Bone Marrow Transplantation, vol. 9 (Suppl. 1): 77–82, Jan. 1992.

*Primary Examiner*—Brian R. Stanton
*Assistant Examiner*—Karen M. Hauda
*Attorney, Agent, or Firm*—Benjamin Aaron Adler

[57] ABSTRACT

The present invention provides a non-human chimeric mammal, comprising a severe-combined immunodeficient mammal engrafted with bovine immune system tissues, wherein said chimeric mammal is functionally reconstituted. Also provided is a method of producing a functionally reconstituted scid-bo mouse with bovine fetal hematopoietic tissues.

6 Claims, 5 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 21
      (B) TYPE: nucleic acid
      (C) STRANDEDNESS: double
      (D) TOPOLOGY: linear    (ii) MOLECULE TYPE:
      (A) DESCRIPTION: other nucleic acid    (iii) HYPOTHETICAL: No    (iv) ANTI-SENSE: No    (vi) ORIGINAL SOURCE:
      (B) STRAIN:
      (C) INDIVIDUAL ISOLATE:
      (D) DEVELOPMENTAL STAGE:
      (F) TISSUE TYPE:
      (G) CELL TYPE:

-continued

```
        (H) CELL LINE:

(xi) SEQUENCE DESCRIPTION: SEQ ID NO:1:

CCCAGCTTTC  CTTCGCAACT  C                                           21

(2) INFORMATION FOR SEQ ID NO:2:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE:
        (A) DESCRIPTION: other nucleic acid (iii) HYPOTHETICAL: No (iv) ANTI-SENSE: No (vi) ORIGINAL SOURCE:
        (B) STRAIN:
        (C) INDIVIDUAL ISOLATE:
        (D) DEVELOPMENTAL STAGE:
        (F) TISSUE TYPE:
        (G) CELL TYPE:
        (H) CELL LINE:

(xi) SEQUENCE DESCRIPTION: SEQ ID NO:2:

GATTCCGGGA  ACTTTGTGGG                                              20
```

FUNCTIONAL RECONSTITUTION OF SCID-BO MICE WITH BOVINE FETAL HEMATOPOIETIC TISSUES

BACKGROUND OF THE INVENTION

1. Field of the Invention

The present invention relates generally to the fields of molecular immunology and the generation of non-human chimeric animals. More specifically, the present invention relates to the functional reconstitution of severe combined immunodeficient (SCID) mice with bovine fetal hematopoietic tissues (scid-bo).

2. Description of the Related Art

High maintenance costs, long gestation periods, uncertain health status, and variable genetic backgrounds limit the utilization of cattle in immunological and infectious disease research. Severe combined immunodeficient (SCID, C.B-17 scid/scid, FOX SCID) mice successfully engrafted with bovine fetal tissues or peripheral blood lymphocytes obviate many of these limitations and provide a smalll animal model for the study of different elements of the bovine immune system.

SCID mice are ideal recipients for tissue xenografts as they lack functional T and B lymphocytes. A variety of species tissues have been used as tissue donors for the development of immunologically chimeric SCID mice including the bovine, equine, feline, porcine, and human tissues. The SCID-human (SCID-hu) chimeric mouse model has greatly facilitated studies of human hematopoiesis, lymphomagenesis, and the immune response to HIV infection.

The prior art is deficient in the lack of effective means of generating functional reconstitution of scid-bo mice with bovine fetal hematopoietic tissues. The present invention fulfills this longstanding need and desire in the art.

SUMMARY OF THE INVENTION

The present invention describes the conditions necessary to reconstitute a bovine immune system in SCID mice which supports the generation of de novo primary and secondary serum antibody responses to a hapten-carrier (DNP-KLH) conjugate. Sublethally irradiated SCID mice were engrafted with fetal bovine liver, lymph node and thymus. Treatment groups were established in which human recombinant interleukin 7, autologous bovine bone marrow, and engraftment site (omentum or abdominal wall) were evaluated for their ability to enhance the reconstitution of the bovine immune system in SCID mice. Seven different fetal tissue donors were utilized (28 mice/donor). Engrafted SCID mice were immunized at approximately 6 and 12 weeks post-engraftment with DNP-KLH. Vaccinated mice were evaluated by ELISA for serum anti-DNP (antigen-specific Ig) and total concentrations of bovine serum immunoglobulin (Ig) biweekly through 20 weeks post-engraftment. SCID mice with fetal tissues engrafted onto the abdominal wall from two different donors produced microgram quantities of bovine Ig and exhibited a greater than 70% reconstitution rate. The administration of human IL-7 and/or fetal bovine bone marrow did not significantly increase the frequency of reconstitution. Subclass analysis of serum from mice receiving the abdominal implants suggested that class-switching occurred from a predominant IgM response after first immunization to a predominant IgG response after the second immunization to DNP. Pooled thymic and splenic lymphocyte populations obtained 20 weeks post-engraftment from abdominally engrafted groups yielded 38–90% bovine cells as determined by PCR in situ hybridization with bovine satellite DNA specific primers. The present invention demonstrates that an antigen-specific bovine immune response to DNP can be measured in heterochimeric SCID-bo mice.

In one embodiment of the present invention, there is provided a non-human chimeric mammal, comprising a severe-combined immunodeficient mammal engrafted with bovine immune system tissues, wherein said chimeric mammal is functionally reconstituted.

In another embodiment of the present invention, there is provided a severe-combined immunodeficient mouse, said mouse having been engrafted with a functional bovine immune system.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 1A & B show a comparison of DNP-specific immunoglobulin levels for donor 5 (FIG. 1A, Ig; FIG. 1B, IgM) in the weeks after post-primary immunization. Symbols: --=graft only; -0-=graft and bone marrow; -Δ-=graft piIL-7; and -◇-=graft plus bone marrow plus IL-7.

FIGS. 2A & B show a comparison of DNP-specific immunoglobulin levels for donor 6 (FIG. 2A, Ig; FIG. 2B, IgM) in the weeks after post-primary immunization. Symbols: - -=graft only; -0-=graft and bone marrow; -Δ-=graft plus IL-7; and -◇-=graft plus bone marrow plus IL-7.

DETAILED DESCRIPTION OF THE INVENTION

Definitions

As used herein, the term "SCID" or "severe combined immunodeficient" means lacking functional T and B lymphocytes.

As used herein, the term "engraft" means placement and attachment by surgical means and/or injection of tissues or cells of a donor animal into or onto a recipient animal.

As used herein, the term "abdomin" and abdominal wall" means the latero-ventral area of the peritoneal cavity of the recipient mouse.

As used herein, the term "reconstitution" or "functional reconstitution" means the ability of the recipient animal to recognize and respond to a foreign antigen de novo.

The present invention is directed to a non-human chimeric mammal, comprising a severe-combined immunodeficient mammal engrafted with bovine immune system tissues, wherein said chimeric mammal is functionally reconstituted. It is expected that the non-human chimeric mammal of the present invention would generate a primary and secondary antibody response when stimulated by a T cell dependent antigen. In a preferred embodiment, the non-human chimeric mammal is a mouse.

Generally, the non-human chimeric mammal of the present invention is engrafted with bovine immune system tissues that are fetal tissues. Representative examples of such bovine immune system tissues include thymus, liver, lymph node and bone marrow. Preferably, these fetal tissues are derived from an animal in early to mid stage second trimester of gestation. As discussed in greater detail below, it is critical to the present invention that the bovine immune system tissues are engrafted into the abdominal wall of the mammal.

The present invention is also directed to a method for the production of the chimeric mammal of claim 1, comprising the steps of preparing the recipient animal presurgically with low dose irradiation and antibody treatments; implanting a second trimester bovine fetal liver, thymus and/or lymph node into the latero-ventral wall of the abdomen of said recepient mouse; and immunizing and screeing said mouse for bovine cells, total immunoglobulin and antigen-specific immunoglobulin.

The present invention also is directed to a severe-combined immunodeficient mouse, said mouse having been engrafted with a functional bovine immune system.

The following examples are given for the purpose of illustrating various embodiments of the invention and are not meant to limit the present invention in any fashion.

EXAMPLE 1

Animals

Homozygous female C.B-17scid/scid mice (FOX SCID) were obtained from Taconic Farms (Germantown, N.Y.) and used at 6–10 weeks of age for engraftment or as control animals. Animals were fed autoclaved food and water and all manipulations other than the engraftment surgery were performed under laminar flow barriers. The mice were divided into 5 groups of at least 24 mice. Groups A and C received fetal bovine thymus, lymph node, and liver tissue engraftments onto the abdominal wall. Groups B and D received fetal bovine thymus, lymph node, and liver tissue grafts in the omentum. Mice in groups C and D also received an intravenous transfer of $1\times10^8$ autologous fetal bovine bone marrow cells intravenously in addition to the fetal tissue grafts noted earlier. All the mice in each group were immunized subcutaneously with 200 μg 2,4 dinitrophenol/keyhole limpet hemocyanin (DNP-KLH) (Sigma, St. Louis, Mo.) in RIBI adjuvant (RIBI Immunochemicals, Hamilton, Mont.) (total volume 100 μl) at 6 and 12 weeks post-engraftment. Group E mice received no treatments and served as controls. All animal experiments were approved by the Institutional Animal Care and Use Committee of the University of Missouri-Columbia and conducted under guidelines established by the University of Missouri System, the U.S. Department of Agriculture, and the National Institute of Health.

EXAMPLE 2

Pre-engraftment Treatments

All mice received sulfamethoxazole/trimethoprim suspension (Biocraft Laboratories, Inc, Elmwood Park, N.J.) in drinking water (40 mg trimethoprim and 200 mg sulfamethoxazole per 320 ml of drinking water) prior to surgery and on alternate days up to 14 days post-operatively. Anti-asialo and radiation treatments were applied to the mice as reported by Shpitz, et al. (*J of Immunol Method.* 169(l) :1–15, (February 1994). Briefly, on the day of surgery all mice received a sublethal dose of whole body gamma irradiation (400 rads). All mice engrafted with fetal tissues received 200 μg doses of rabbit anti-asialo GM1 antisera (Wako Chemicals, Inc., Dallas, Tex.) intraperitoneally in Hank's buffered salt solution, pH 7.2 (HBSS) to augment depletion of resident murine NK cells and macrophages. Serial doses of rabbit anti-asialo GM1 antisera were given one to two days before surgery and at weekly intervals up to one month following surgery.

EXAMPLE 3

Engraftment Procedure

Anesthesia was induced with intraperitoneally administered ketamine hydrochloride (Ketaset, Fort Dodge Laboratories, Inc., Fort Dodge, Iowa) (0.05 mg/g body weight) and maintained with isofluorane, USP, (Aerrane, Anaquest, Madison, Wis.) delivered via a mask apparatus. The anesthetized mice were positioned in dorsal recumbency and surgically draped (Avian Drapes, General Econopak, Inc., Philadelphia, Pa.). All procedures were performed utilizing standard aseptic surgical techniques. A 2-cm midline ventral abdominal incision was made exposing the peritoneum and omentum. Prepared pieces of bovine fetal thymus, liver, and lymph node were threaded onto 5-0 nylon sutures (Ethilon, Ethicon, Inc., Somerville, N.J.) and the fetal tissues were oversewn into a cranial ventral segment of the omentum or tacked onto the peritoneal surface of the left lateroventral abdominal wall. The abdomen was closed with 5-0 nylon sutures. Buprenorphine hydrochloride (Buprenex, Reckitt and Colman Pharmaceuticals, Inc., Richmond, Va.) was administered subcutaneously (0.2 mg/100 grams body weight) for post-operative analgesia.

EXAMPLE 4

Fetal Tissues

Fetal liver, thymus, lymph node, and bone marrow were obtained from five second trimester cross-bred bovine fetuses (Pel Freeze, Inc, Rogers, Ark.). Fetal bovine tissues were collected aseptically into RPMI containing 4 μg gentamycin sulfate (Fermenta Animal Health Co, Kansas City, Mo.) and engrafted within 18 hours of collection. Tissues were sized (approximately 2 $mm^3$) for engraftment using a sterile scalpel blade.

One half of the animals in each treatment group received recombinant human interleukin 7 (rhIL-7) as a hematopoeitic growth factor. rhIL-7 recipients were coimplanted with an Alzet micro-osmotic pump model 1007D (Alza Corp., Palo Alto, Calif.) adjacent to the graft (flow rate=0.5 m 1/hr, 7 days). The concentration of IL-7 (100 ng/ml) used was determined empirically from in vitro studies in both human and mouse bone marrow cultures.

EXAMPLE 5

Bone Marrow

Approximately $1\times10^7$–$1\times10^8$ bovine bone marrow (BM) cells were infused intravenously via the tail vein into appropriate experimental groups. The bone marrow cells were from syngeneic fetal femoral bone marrow plugs (Pel Freeze, Inc, Rogers, Ark.). The plugs were cored with an 18 gauge needle and washed with RPMI solution. Washings were strained through a 70 μm cell strainer (Becton Dickinson Labware, Franklin Lakes, N.J.) to remove aggregates. Cells ($2\times10^9$ cells/ml) were then rinsed twice in HBSS (Becton Dickinson Labware, Franklin Lakes, N.J.) and 50 μl were transfused.

EXAMPLE 6

ELISA

Engrafted and control mice were bled every two weeks post immunization from the retro-orbital venous sinus for assessment of serum levels of bovine and 2, 4-DNP specific immunoglobulin (Ig). All immunologic reagents were tested for cross-reactivity to mouse serum proteins. Those demonstrating cross-reactivity were absorbed using a mouse serum agarose column (Sigma). Sheep anti-bovine IgM and IgG (H+L) (The Binding Site; San Diego, Calif.) were extensively absorbed against mouse serum proteins to remove any residual species cross-reactivity. A capture ELISA similar to a murine isotype assay previously described (Estes et al., Cellular Immunology, 54:287–295, 1994) was developed for quantitation of bovine isotypes. Briefly, ELISA plates were coated with 100 μl of 10 μg/ml goat anti-mouse IgG(H+L) and then blocked for 1 hour at 37° C. with 5% horse serum (Gibco-BLR; Gaithersburg Md.) in phosphate-buffered saline. Dilutions (1:100–1:500) of serum samples were incubated for 1–2 hours, washed, and then biotinylated sheep anti-bovine class-specific reagents were added. The humoral response to (DNP-KLH) (Sigma) was determined by direct ELISA with antigen-coated plates (1 μg/well). Plates were developed using biotinylated isotype-specific sheep anti-bovine antisera and substrate as described for the capture assays. KLH was haptenated with DNP and purified as previously described by Hudson L., Practical Immunology, Practical Immunology, Blackwell Scientific Publications, Boston, p. 5–7, 1980.

EXAMPLE 7

Polymerase Chain Reaction in situ Hybridization (PISH)

Splenic and thymic lymphocytes from mice with detectable bovine serum Ig at 8 weeks post-engraftment were analyzed for the presence of bovine satellite DNA on a per cell basis in splenocytes and thymocytes by a modification of a previously described technique of Nuovo, G. J., PCR in situ hybridization., Raven Press, New York, 1992. Specific primers which amplified chromosomal regions with bovine and not mouse satellite DNA were used. The primer set showed minimal cross-reactivity with endogenous mouse DNA. The primers utilized were BTSATI forward (5'-CCCAGCTTTCCTTCGCAACTC-3') and BTSATI reverse (5'GATrCCGGGAACITGTGGG-3').

For PISH, single cell suspensions in HBSS were obtained from the thymus and spleens of mice following exsanguination weeks post-engraftment. Cells were spun down onto slides ($5\times10^4$ cells per slide) using a cytospin centrifuge (Shandon, Inc., Pittsburgh, Pa.) and fixed with 10% buffered formalin overnight. Slides were stored in 70% ethanol until assayed. Genecones (Gene Tec Corp., Durham, N.C.) were applied over the cell button, fixed, and then loaded with PCR reaction mix according to manufacturer's instructions (DNA PCR Kit, Perkin-Elmer Cetus, Emeryville, Calif.). Digoxigenin labeling mix (Boehringer Mannheim, Indianapolis, Ind.) replaced the single nucleotides in the kit. Slides were placed on a tempcycler (TempTronic, Barnstead/Thermolyne Corp., Dubuque, Iowa) and processed by hot start PCR (start cycle, 80° C. for 8 minutes; 40 cycles, melting 95° C. for 1 minute; annealing, 55° C. for 1 minute; extension, 72° C. for 1.5 minutes).

After PCR amplification, Genecones were removed and slides were washed twice in Buffer A (0.1 M NaCl, 2 mM $MgCl_2$, 0.1 M Tris, pH 7.5, 0.05% Triton X-100) in a humid chamber. Slides were then blocked (30 minutes, room temperature) in buffer A containing 2% bovine serum albumin, and washed twice in buffer A for 5 minutes. Alkaline phosphatase-labeled anti-digoxigenin (Fab')2 fragments (Boehringer Mannheim) were added and slides diluted 1:500 in buffer A containing 1% BSA (Sigma) were incubated for 2 hours. Following a series of washes in buffer A solution, slides were washed in Buffer B (0.1 M Tris, pH 9.5, 0.1 M NaCl, 0.05 M $MgCl_2$). Slides were then incubated in substrate (5-bromo-4-chloro-3-indoyl-phosphate/nitro blue tetrazolium, BCIP/NBT, Promega, Madison, Wis.) and incubated overnight in the dark. The slides were washed and counterstained with nuclear fast red (Sigma). Slides containing 100% mouse spleen cells (BALB/cJ, Jackson Laboratories, Bar Harbor, Me.) or 100% bovine peripheral blood T-cells) were used as negative and positive controls respectively. The bovine peripheral blood T-lymphocytes were obtained from a 1 year old Holstein steer as previously described by Estes, et al., Cellular Immunology, 154:287–295, 1994.

EXAMPLE 8

Microscopic Analysis

Engraftment sites were collected at necropsy and fixed in 4% paraformaldehyde for 1 hour. They were stored in 40% aqueous sucrose until processed for cryostat sectioning, staining with hematoxylin/eosin, and light microscopic analysis.

EXAMPLE 9

Total Bovine Serum Ig Levels in SCID-bo Heterochimeric Mice

Figure 1A:
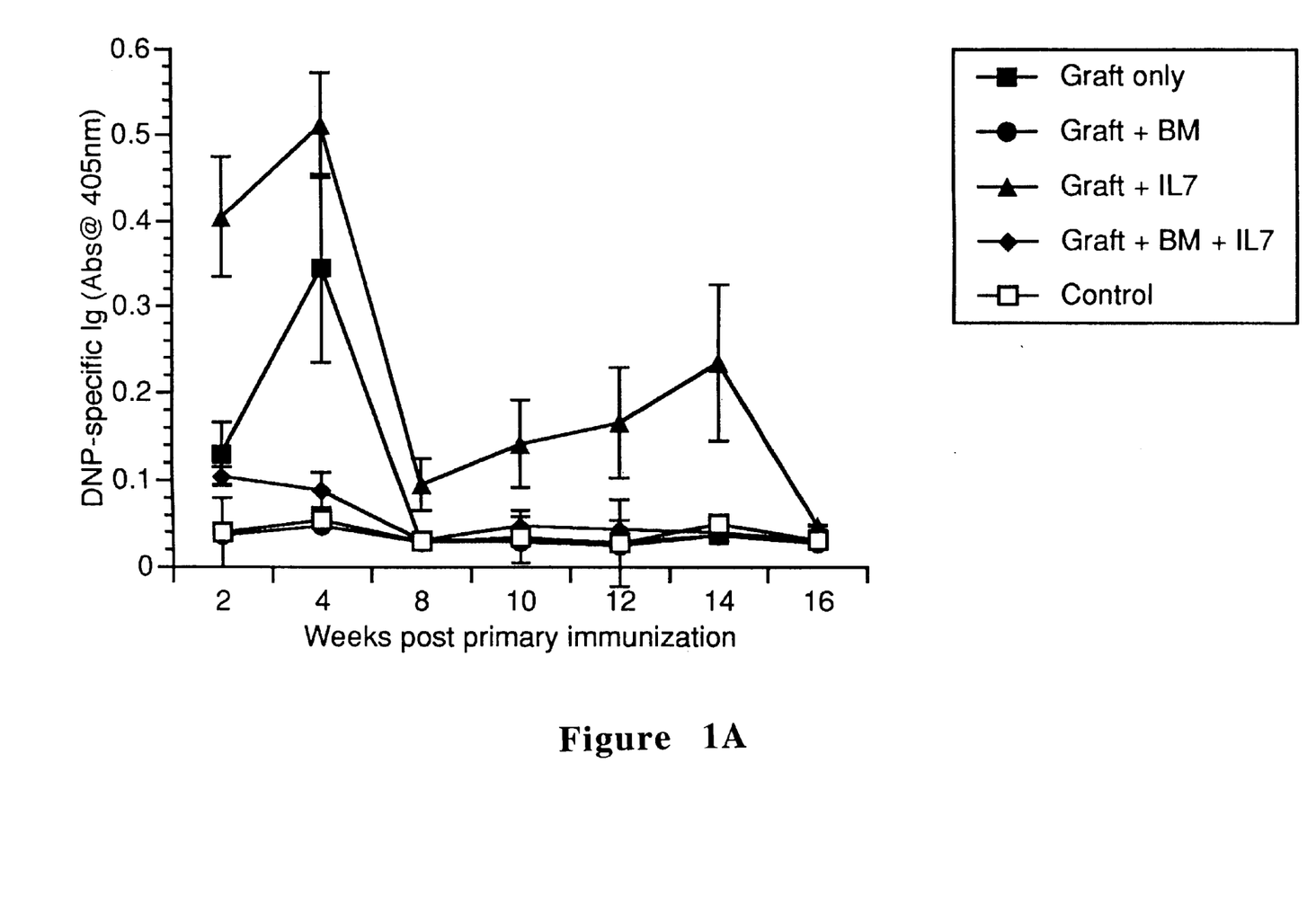
Figure 1B:
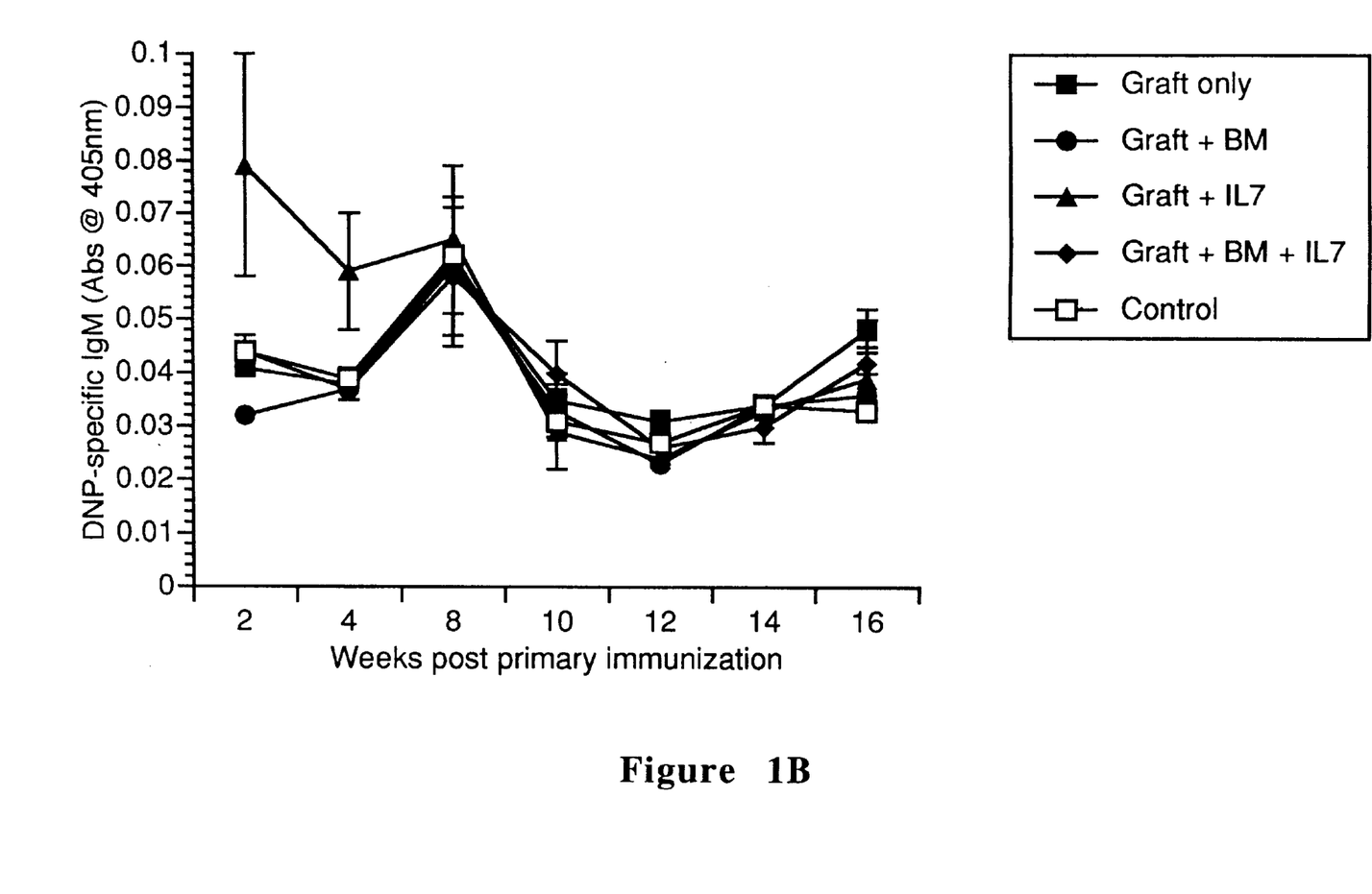
Figure 2A:
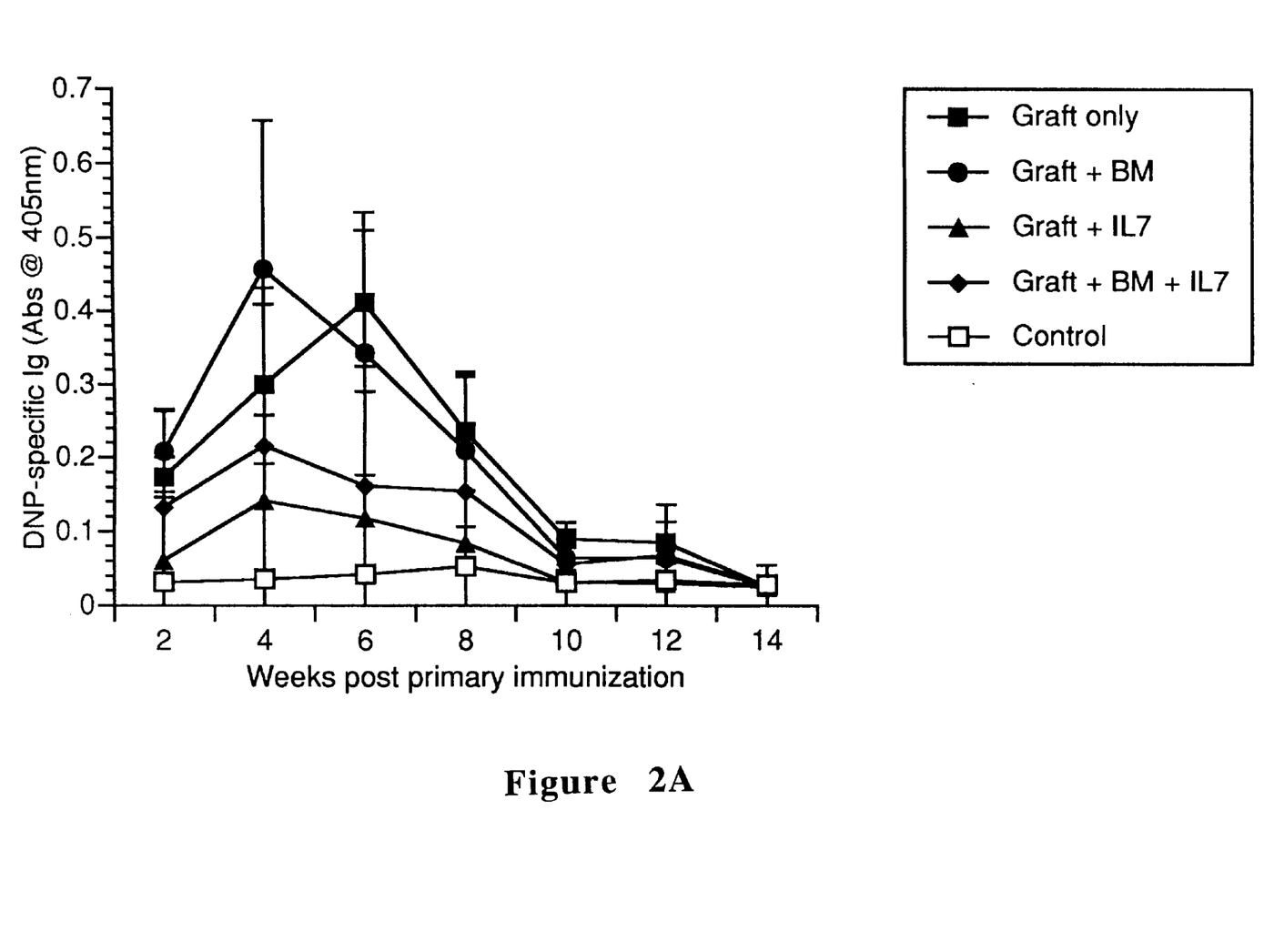
Figure 2B:
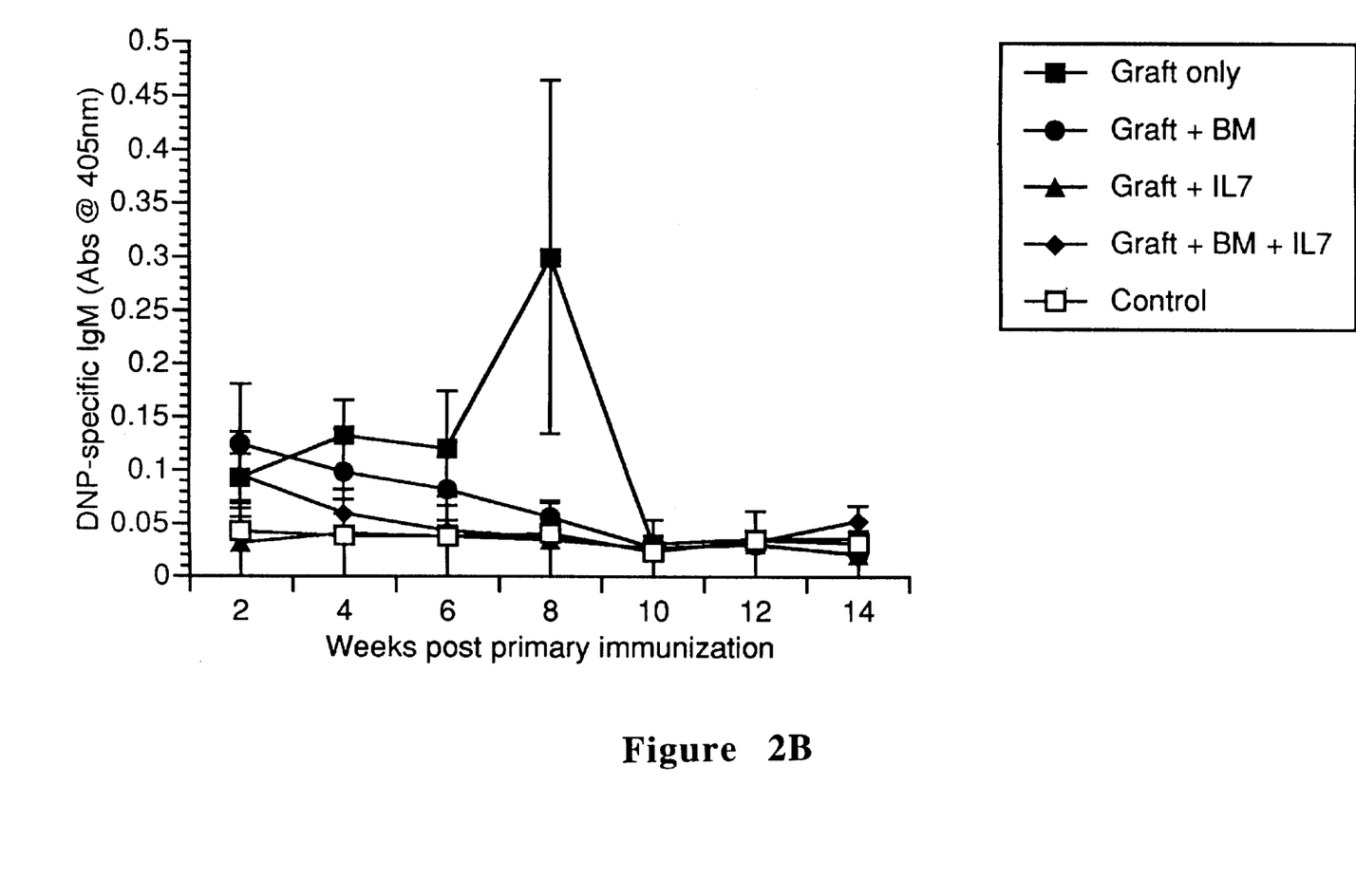

SCID-bo mice engrafted with bovine tissues in either the omentum (data not shown) or abdominal wall placement sites possessed nanogram to microgram quantities of total bovine immunoglobulin (Ig) per ml serum at 8 weeks post immunization (data not shown). Subclass analysis of serum indicated that both bovine IgM and IgG isotypes were present in heterochimeric mice receiving abdominal wall engrafted tissues from Donor 6 two weeks after primary immunization with DNP-KLH in RIBI adjuvant (TABLE I; FIGS. 1 and 2). After secondary exposure to DNP-KLH in RIBI adjuvant the total bovine serum antibody profile in these mice shifted from IgM and non-IgM isotypes to predominantly non-IgM isotypes (TABLE I; FIGS. 1 and 2). Total serum Ig levels in SCID-bo mice with tissues from donors 5 and 6 engrafted on the abdominal wall were estimated to be in microgram per milliliter quantities of serum for the duration of the study. These estimates were based on comparison of ELISA absorbance readings on bovine isotype standards by linear regression analysis (data not shown).

TABLE 1

Total Bovine Immunoglobulin[a] in Site C engrafted SCID-bo mice

| | Ig (R)[b] | IgM (R) |
|---|---|---|
| Study I (Donor 5) | 2 weeks post-immunization | |
| Graft only (n = 9) | 74 ± 8 (6) | — |
| Graft + BM (n = 5) | — | — |
| Graft + IL-7 (n = 6) | 81 ± 7 (5) | — |
| Graft + BM + IL-7 (n = 7) | 58 ± 12 (4) | — |
| Study II (Donor 6) | | |
| Graft only (n = 4) | 103 ± 11 (4) | 12 ± 6 (2) |
| Graft + BM (n = 5) | 116 ± 10 (3) | 29 ± 4 (1) |
| Graft + IL-7 (n = 4) | 98 ± 9 (3) | — |
| Graft + BM + IL-7 (n = 8) | 100 ± 11 (6) | 66 ± 12 (1) |
| Study I (Donor 5) | 2 weeks post-booster immunization | |
| Graft only (n = 9) | 52 ± 4 (6) | — |
| Graft + BM (n = 5) | 25 (1) | — |
| Graft + IL-7 (n = 6) | 78 ± 6 (4) | — |
| Graft + BM + IL-7 (n = 7) | 66 ± 15 (3) | — |
| Study II (Donor 6) | | |
| Graft only (n = 4) | 97 ± 17 (3) | 14 (1) |
| Graft + BM (n = 5) | 82 ± 34 (3) | — |
| Graft + IL-7 (n = 4) | 35 ± 9 (3) | — |
| Graft + BM + IL-7 (n = 8) | 99 ± 19 (6) | — |

[a]refers to total bovine immunoglobulin (Ig) and IgM levels determined by capture ELISA absorbance values relative to bovine isotype standards. Values are reported in micrograms per ml.
[b]refers to (R) = number mice per treatment group producing detectable levels of Ig.

EXAMPLE 10

DNP-Specific Bovine Serum Ig Levels in SCID-bo Heterochimeric Mice

Serum antibody responses to DNP-KLH were evaluated by antigen-specific ELISA. Absorbance values obtained at serum dilutions of 1:100 - 1:500 indicated that levels of DNP-KLH-specific Ig were negligible in preimmune serum samples from all mice tested and relative to pooled control sera from nonengrafted SCID mice. SCID-bo mice implanted with fetal lymph node, thymus, and liver tissues from two different donors were inoculated with DNP-KLH. Retrospective evaluation of bovine Ig specific for DNP-KLH over the course of antigenic stimulation by ELISA indicated significant increases in ELISA absorbance values for antigen-specific antibody over those seen in all other control and engrafted groups (mean+standard deviation). These observations were correlated with the generation of a primary antibody response to antigen based on isotype analysis for two separate fetal tissue donors (FIGS. 1 and 2).

C.B-17 scid/scid mice receiving abdominal wall placement of fetal lymph node, thymus, and fetal liver tissues with co-administration of autologous bone marrow had lower rates of reconstitution than all the other treatments (p<0.01) (Table 2). As determined by anti-DNP-KLH serum bovine Ig concentrations at 8 weeks post engraftment, administration of rhIL-7 directly into the graft site via mini-osmotic pump did not significantly alter rates of reconstitution, and infusion of bone marrow cells did not affect this outcome (p<0.34) (Table 2).

TABLE II

Effect of graft composition, engraftment site, and cytokine treatment on reconstitution rates of C.B/17-scid/scid mice

| | % reconstituted[a] | | | |
|---|---|---|---|---|
| | Graft Site B | | Graft Site C | |
| Treatment Group | Donor 2 | Donor 4 | Donor 5 | Donor 6 |
| Graft only | 0 (0/6) | 0 (0/6) | 67 (6/9) | 100 (4/4) |
| Graft + bone marrow | 0 (0/3) | 0 (0/3) | 0 (0/5) | 60 (3/5) |
| Graft + IL-7 | 0 (0/6) | 0 (0/3) | 83 (5/6) | 75 (3/4) |
| Graft + bone marrow + IL-7 | 0 (0/3) | 0 (0/3) | 57 (4/7) | 75 (6/8) |

[a]Reconstituted means the mouse has serum DNP-specific bovine immunoglobulin levels exceeding that of control SCID mice (mean + 2 standard deviations)

EXAMPLE 11

Polymerase Chain Reaction in situ Hybridization (PISH)

Pooled cytospin preparations of cells from the spleen and thymus of SCID-bo mice were analyzed by PISH using bovine satellite DNA-specific primers to determine the proportion of bovine and mouse cells on a per cell basis. Assay conditions were optimized with bovine-specific oligonucleotide primers prior to analysis of SCID-bo mice using known proportions of bovine peripheral blood lymphocytes (PBL's) and mouse splenocytes. Splenocytes and thymocytes from reconstituted mice were evaluated in parallel with positive (bovine T cells) and negative (mouse spleen cells) control slides by PISH for the presence or absence of bovine DNA. Splenocyte preparations from three groups of variably reconstituted mice ranged of from 77–90% positive cells with respect to presence of bovine satellite DNA (Table 3). Evaluation of species DNA content from thymocyte preparations from these same groups yielded a range of 38–70% positive cells (Table 3).

TABLE III

Lymphoid Tissue Cells Expressing Bovine Satellite DNA Sequences

| | % positive cells[b] | |
|---|---|---|
| | Spleen Cells | Thymus cells |
| Treatment (donor 5) | | |
| Graft only | 77 | 49 |
| Graft + bone marrow | n.d. | n.d. |
| Graft + IL-7 | 90 | 70 |
| Graft + bone marrow + IL-7 | 86 | 38 |
| Controls | | |
| Positive-bovine PBMC | >95 | |
| Negative-BALB/c splenocytes | <1 | |

EXAMPLE 12

Microscopic Analysis of Graft Sites

Only two of thirteen graft sites obtained 18 weeks post-engraftment contained detectable remnants of the engrafted tissues (2 lymphoid tissue masses, data not shown). The remaining grafts examined contained a dense fibrous tissue mass, no inflammatory cell response was noted.

EXAMPLE 13

Construction of SCID-bo Mice

Homozygous female C.B-17 scid/scid beige mice (Harlan Sprague-Dawley) were utilized at 6–10 weeks of age for engraftment or as control animals. Prior to surgery, the mice received trimethoprim-sulfa suspension (4 mg/5 ml suspension added 1:32 in drinking water) and on alternate days up to 14 days post operatively. Bovine fetal liver, thymus, and lymph node were obtained from second trimester cross-bred fetuses by Pel Freeze, Inc. (Rogers, Ark.). Tissues were obtained aseptically and collected into RPMI containing gentamicin sulfate and engrafted within 18 hours of collection. Tissues were sized into 0.5–1.0 cm pieces and implanted onto the latero-ventral abdominal wall.

Pasteurella hemolytica Biotype A1 originally isolated from the lung of a calf with pneumonia was maintained as a frozen culture at −70° C. This strain contains an ampicillin resistance plasmid for epidemiological identification. All culture procedures were done with standard bacteriological methods using brain heart infusion agar supplemented with 5% bovine blood and 1% filtered yeast hydrosylate (BHIBA). Incubation was at 37° C. under 5% $CO_2$. Inocula were prepared using log phase confluent growth suspended in phosphate buffered saline (PBS, pH 7.2) at $10^8$–$10^9$ CFU/ml.

For an intratracheal challenge of SCID-bo mice with Pasteurella hemolytica Biotype A1, sodium pentobarbital was used for anesthesia at a 1:8 dilution in sterile water from a 50 mg/ml stock solution. Mice (N=3 per treatment group) received 150 microliters of anesthetic intraperitoneally prior to challenge. Each mouse was placed in dorsal recumbency once immobilized and a longitudinal incision was made through the skin and through the ventral surface of the trachea large enough to accomodate a 20 g needle as previously described (Pace et al., Can. J. Vet. Res. 58:79–82, 1994). Twenty-five microliters of inoculum was used per mouse in both normal SCID (control animals, N=3) and SCID-bo mice (N=3). The mice were kept warm under a heat lamp until fully recovered from anesthesia. Mice were sacrificed at 24 hours post challenge and lung tissue collected for quantitative bacteriology to determine CFU per gram of lung tissue and gross and histologic pathology.

Figure 3:
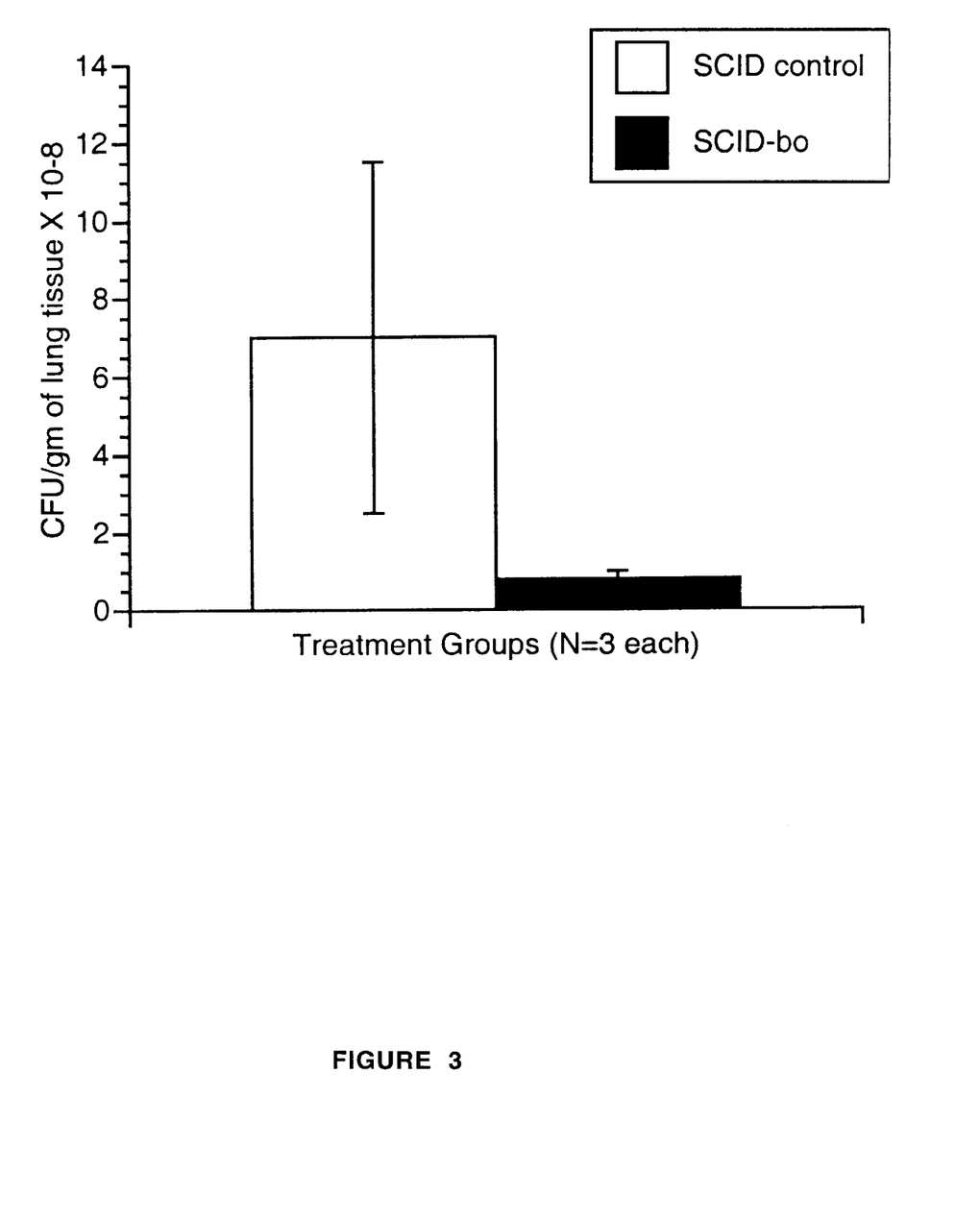
FIG. 3 shows the amounts of colony forming units in the lung 24 hours following intratracheal challenge of SCID and SCID-bo mice with *Pasteurella hemolytica* biotype A1. Mice were challenged at 8 weeks post engraftment (SCID-bo) with age matched unengrafted control C.B.17 scid/scid mice with 108 CFU of organism in 25 milliliters of saline. Lungs were harvested at necropsy and mechanically processed to disrupt the lung tissue into a single cell suspension. Supernatants were harvested from disrupted tissue following homogenization and centrifugation and bacteria plated in serial log dilutions on selective media. Results are depicted as the mean and standard error for three mice per group.

Quantitative bacteriologic determinations of bacterial load in the lungs of SCID and SCID-bo mice are shown in FIG. 3. Results are depicted as colony forming units of bacteria (CFU) per gram of lung tissue homogenate. SCID-bo mice demonstrated approximately 33 fold lower levels of bacteria in the lung at 24 hours post challenge relative to control SCID mice, indicating that these mice are reconstituted with a functional bovine immune system. Although not directly demonstrated, multilineage reconstitution can be inferred from these data as both neutrophil and macrophage lineages are critical to resistance to challenge at the time point tested in this study. Importantly in doubly deficient recipient SCID-beige mice, resident mouse neutrophils are inactive due to a genetic defect which alters the ability of these mice to degranulate. This mutation also affects NK cells to kill the appropriate target cell. Therefore, resident murine NK or neutrophils were unable to contribute functionally to anti-bacterial resistance.

In the present invention, the ability of various treatment and engraftment regimens to enhance the reconstitution success of fetal bovine hemato-lymphoid tissues in SCID mice was demonstrated. Interleukin-7 promotes the proliferation and differentiation of pre-B and pre-T cells in long-term bone marrow culture and in thymocyte development, respectively. In the present invention, rhIL-7 at the concentration and time course utilized did not significantly increase reconstitution rates of the bovine immune system in the SCID mouse. Species cross-reactivity of rhIL-7 in bovine systems has not been established but was inferred from the known cross-reactivity of human IL-7 on murine pre-B cells. It is possible that alternative doses of rIL-7 would augment reconstitution rates and efficiencies.

In a SCID-hu model system, addition of human fetal liver to SCID mice co-engrafted with thymus and lymph node resulted in detectable circulating human lymphocytes up to one year post-engraftment, suggesting active hematopoiesis via the introduction of liver-derived human pluripotent stem cells. The present invention demonstrates that both the choice of tissues as well as selection of engraftment site are key to enhancing success rates and levels of reconstitution of SCID mice with functional bovine B and T lymphocytes. At present, the precise basis for the relatively high success rate of this graft site is unclear. Analysis of graft sites at the time of necropsy indicated that while in most cases the precise engraftment site was traceable due to the presence of residual suture material, the fetal tissue tricomplex (fetal liver, thymus, and lymph node) was virtually undetectable, due presumptively to tissue absorption in the abdominal wall. Abdominal wall placement of graft material offers several advantages, both in terms of the ease of surgical manipulation and reduced trauma, as well as possible rapid revascularization of graft material.

C.B-17 scidlscid mice possess normal to slightly elevated levels of NK activity when compared to normal C.B-17 and BALB/c mice. As NK cells are known mediators of graft rejection, a variety of studies have examined strategies to enhance reconstitution via elimination or reduction of this cell population. Pretreatment of SCID mice with anti-asialo GM1 antisera and low dose irradiation enhances reconstitution efficiencies in studies with human hematolymphoid cells in C.B-17 scid/scid mice. Although C.B-17 scid/beige mice have 50% fewer NK cells than normal SCID mice, the administration of rabbit anti-asialo GM1 antisera has been shown to prolong the production of human lymphocytes from fetal lymph node grafts in the SCID-hu model to over one year post-reconstitution. Pretreatment of C.B-17 scidiscid mice with irradiation has not been shown to enhance adult bovine-PBL-SCID reconstitution rates, whereas other studies have demonstrated improved capability to elicit both primary and secondary immune responses in adoptive transfer studies of human PBL's in anti-NK pretreated SCID mice.

Previous reports in SCID-bo mice demonstrated decreased to non-detectable bovine Ig levels by 8–10 weeks post-engraftment suggesting that the bovine Ig observed originated from resident Ig-secreting B-cells in the fetal graft material at the time of engraftment. This observation was based on the half-life of bovine Ig in the SCID mouse which has been estimated at 10.5 days. Previous ontogenic studies have identified IgM-bearing lymphocytes as early as the 59the day of gestation and secretory IgM in the serum at 145 days. Fetal tissues used herein were obtained from early to mid stages of the 2nd trimester. The present invention shows that the detection of bovine Ig utilizing a kidney capsule placement site was dependent on obtaining grafts less than 17 weeks of gestation.

The proportions of bovine lymphocytes in the spleen and thymus of SCID-bo mice at over 140 days post-engraftment were significantly higher than that observed in studies using kidney capsule placement of bovine fetal tissues. While others have used soluble DNA content to estimate the frequencies of xenogenic cells relative to mouse cells by PCR in SCID heterochimeric mice, the present invention describes procedures wherein the frequency of bovine cells on a per cell basis is determined directly by polymerase chain reaction in situ hybridization. Importantly, the present invention shows a direct correlation in the ability to detect antigen-specific antibody responses of the species of origin of the tissue donor to the proportion of those cells in various lymphoid compartments.

Given the relatively low frequency of antigen-specific cells in normal individuals ($1:10^4$–$1:10^5$), functional reconstitution of tissue donor lymphocyte function in SCID mice by xenotransplantation requires that the efficiency of engraftment be relatively high in order for antibody or T cell responses to specific antigens to reach detectable limits. Prior studies have indicated that generalized reconstitution in terms of polyclonal Ig production in serum is achievable with many species and that incompatibility of various mammalian cells or tissues with the mouse microenvironment does not contribute to lack of functionality.

In the present invention, various engraftment parameters were examined, alone and in combination, to demonstrate reconstitution efficiencies at the tissue level on a per cell basis in individual mice and serologically by antigen-specific ELISA. The parameters tested included graft site, a hematopoeitic growth factor (recombinant human IL-7, rIL-7), bone marrow stromal cells, as well as low dose irradiation/antibody treatment to eliminate or reduce endogenous NK cell activity. The contribution of donor variability was assessed by evaluating at least two fetal tissue donors per variable combination tested. Taken together, the present invention demonstrates that the key factor in reconstitution of SCID mice with a functional bovine immune system, in terms of ability to generate a primary and secondary antibody response to a T-dependent antigen, is clearly correlated with a specific graft site (abdominal wall). Additional factors such as rIL-7 administration or the co-transfer of bone marrow cells intravenously did not significantly alter outcome. The present invention is the first report of the generation of a de novo antigen specific antibody response in SCID-bo heterochimeric mice.

The present invention has utility for investigating basic immune mechanisms in cattle and will also allow the evaluation of genetic contributions to natural immunity in the absence of both environmental and genetic variability. Moreover, the costs associated with generating and maintaining these mice are much less than those required for performing similar studies in research cattle.

The SCID-bo mouse of the present invention have further utility such as in vaccine trials where it is difficult and expensive to conduct such trials in large animals due to the housing/acquisition costs and the undefined health status of research cattle. In the area of genetic testing, resistance or susceptibility to infectious disease or etiologic agents can be tested in mice which are reconstituted from a single donor and thus are genetically identical. Thus, breeders and geneticists will be able to identify putative immune response genes which correlate with resistance or susceptability to disease and/or vaccine failure, i.e., non-responders. In the area of nutritional or toxicological studies, testing of various feed supplements, e.g., Vitamin A, on the developing immune system can be conducted.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A severe-combined immunodeficient chimeric mouse, engrafted with bovine immune system tissues, selected from the group consisting of fetal thymus, fetal liver, fetal lymph tissue and fetal bovine bone marrow surgically implanted into the latero-ventrall wall of an abdomen of said-mouse wherein immunity of said mouse is functionally reconstituted.

2. The severe-combined immunodeficient chimeric mouse of claim 1, wherein said mouse generates a primary and secondary antibody response when stimulated by a T-cell dependent antigen.

3. The severe-combined immunodeficient mouse of claim 1, wherein said fetal tissues are obtained from an animal in early to mid stage second trimester of gestation.

4. A method for the production of the severe-combined immunodeficient chimeric mouse of claim 1, comprising the steps of:

(a) preparing a recipient mouse presurgically with low dose irradiation and antibody treatments;

(b) surgically implanting a second trimester bovine tissue selected from the group consisting of fetal bovine bone marrow, fetal liver, fetal thymus and fetal lymph tissue into the latero-ventral wall of an abdomen of said recipient mouse;

(c) immunizing said mouse with an antigen; and (d) screening said mouse for bovine cells, total immunoglobulin and antigen-specific immunoglobulin, wherein a presence of said bovine cells, total immunoglobin and antigen-specific immunoglobin indicates production of said severe-combined immunodeficient chimeric mouse and an absence of said bovine cells, total immunoglobin and antigen-specific immunoglobin indicates that said severe-combined immunodeficient chimeric mouse was not produced.

5. A severe-combined immunodeficient chimeric mouse produced by the method of claim 4, wherein said mouse generates a primary and secondary antibody response when stimulated by a T-cell dependent antigen.

6. A severe-combined immunodeficient chimeric mouse produced by the method of claim 4, wherein said fetal tissues are obtained from an animal in early to mid stage second trimester of gestation.

* * * * *